United States Patent [19]

Block et al.

[11] Patent Number: 5,066,224
[45] Date of Patent: Nov. 19, 1991

[54] ORTHODONTIC ANCHOR

[75] Inventors: Michael S. Block, Metairie; David R. Hoffman, Mandeville, both of La.

[73] Assignee: Oasis Implants Incorporated, Metairie, La.

[21] Appl. No.: 659,680

[22] Filed: Feb. 25, 1991

[51] Int. Cl.[5] ................................. A61C 3/00
[52] U.S. Cl. .................................. 433/7; 433/18; 433/24
[58] Field of Search ................ 433/2, 7, 18, 23, 24

[56] References Cited

U.S. PATENT DOCUMENTS

| | | | |
|---|---|---|---|
| 4,024,638 | 5/1977 | Linkow et al. | 433/176 |
| 4,571,178 | 2/1986 | Rosenberg | 433/7 X |
| 4,592,725 | 6/1986 | Goshgarian | 433/7 |
| 4,988,292 | 1/1991 | Rosen | 433/173 X |

FOREIGN PATENT DOCUMENTS

| | | | |
|---|---|---|---|
| 2425842 | 1/1980 | France | 433/8 |
| 129955 | 10/1950 | Sweden | 433/18 |

OTHER PUBLICATIONS

Sherman, A. J.: Bone Reaction to Orthondontic Forces on Vitreous Carbon Dental Implants, Am. J. Orthod., 74:79-87, 1978.
Smith, J. R.: Bone Dynamics Associated with the Controlled Loading of Bioglass-Coated Aluminum Oxide Endosteal Implants, Am. J. Orthod., 76:618-636, 1979.
Turley, P. K. et al., The Loading of Bioglass-Coated Aluminum Oxide Implants to Produce Sutural Expansion of the Maxilliary Complex in the Pigtail Monkey, Arch. Biol., 25:459-464, 1980.
Gray, J. B.: Studies of the Efficacy of Implants as Orthodontic Anchorage, Am. J. Orthod., 83:311-317, 1983.
Roberts, W. E. et al., Osseous Adaptation to Continous Loading of Rigid Endosseous Implants, Am. J. Orthod., 86:95-111, 1984.
Neary, J. P. et al., A Comparison of Orthodontic Spring Loading of Hydroxlapatite Coated and Grit Titanium Implants in Dogs, AAOMS Annual Scientific Sessions, Boston, Mass., Sep. 1988.
Smalley et al., Osseointegrated Titanium Implants for Maxillofacial Protraction in Monkeys, Am. J. Orthod. Dentofac. Orthop., 94:285-295, 1988.
Block et al., Canine Mandibular Response to Surface-Textured Hydroxylapatite Blocks, Int. J. Oral Maxillofac. Surg., 17:358-359, 1988.
Benjamin et al., Histologic Evaulation of a Retrieved Human Hydroxlapatite Coated Subperiosteal: Report of a Case, Int. J. Oral and Maxillofac. Implants, 4:63, 1989.
Cook et al., Interface Mechanics and Histology of Titanium and Hydroxylapatite Coated Titanium for Dental Implant Applications, Int. J. Oral Maxillofac. Implants, 2:15-22, 1987.
Thomas et al., The Effect of Surface Macrotexture and Hydroxylapatite Coating on the Mechanical Strength and Histologic Profile of Titanium Implant Materials, J. Bio. Mat. Res., 21:1395, 1987.
Block et al., The Effect of Diameter and Length of Hydroxlapatite Coated Dental Implants on Ultimate Pullout Force in Dog Aveolar Bone, J. Oral Maxillofac. Surg., 48:174-178, 1990.

*Primary Examiner*—Robert P. Swiatek
*Assistant Examiner*—Nicholas D. Lucchesi
*Attorney, Agent, or Firm*—Beveridge, DeGrandi & Weilacher

[57] ABSTRACT

An orthodontic anchor system 20 for treatment of growth disharmony and malalignment of teeth in which one element is surgically placed in a subperiosteal tunnel on the skeletal bone, allowing biointegration between the onplant bone interface 30 and the bone, after which a palatal bar 24 is attached to the orthodontic anchor system 20, and the palatal bar 24 is also attached to bands 25 around two teeth, holding them non-mobile, permitting the orthodontist to treat the malalignment of the teeth.

4 Claims, 2 Drawing Sheets

ORTHODONTIC ANCHOR

BACKGROUND OF THE INVENTION

Skeletal deformities become evident during the growth of an individual. Often the earliest signs of maxillary or mandibular growth disharmony is dental malalignment. Once recognized, it is possible to guide the growth of segments of the cranio-facial skeleton in order to minimize the need for surgical correction of the deformity.

Maxillary hypoplasia exists in all three dimensions. Transverse deficiency of the maxilla is often treated by the orthodontist with orthopedic palatal expansion. Deficiency in the maxillary in the vertical or anterior-posterior direction has not been satisfactorily cured by non-surgical guided movements because of a lack of a stable or non-mobile anchorage source for orthopedic movements.

Mandibular deficiency can be corrected by functional appliances which position the mandible forward, and presumably allow for posterior condylar appositional growth which stabilizes the mandible in this forward position. Orthodontists employ orthopedic traction in all three dimensions to control or direct the development of a bone to a favorable location.

Cleft palate patients often have transverse, anterior-posterior, and vertical dysplasia. Reconstruction of these patients often involves orthodontic alignment of the segments prior to bone grafting the defects. However, the defects can be large and difficult to manage when the patient is young. The deciduous dentition can also be difficult to manage in regards to orthodontic anchorage preventing definitive alignment of the arches until the patient is in the early teens.

All orthodontic forces adhere to Newton's Law of Reciprocal Forces. If a force is applied to retract, or pull back, a tooth there exists an "equal and opposite" force to move another tooth forward. The resistive value of the posterior teeth is known as anchorage. Orthodontists offset these reciprocal tendencies by using an extraoral force known as a headgear to augment the resistive value of the molar teeth. However, patient compliance may be poor because many patients do not want to wear the headgear, compromising orthodontic therapy and often the final result.

The problem is that the retractive forces are usually continuous, acting 24 hours a day. Realistically most patients will not wear a headgear more than 10-12 hours a day. Therefore, the posterior anchorage is typically fortified 40-50% of the time. All too often inconsistent usage or overt non-compliance reduce this effect even more.

Previous work in this field indicates that endosseous implants can be used to anchor orthodontic forces for tooth movement. These studies indicate that osseointegrated implants have been used to anchor realignment of teeth, without moving the implants. These implants were placed into the bone.

Clinically, hydroxylapatite coated cylindrical implants have been used since July 1984. Solid blocks of dense hydroxylapatite are available for interpositional and onlay grafting of defects during orthognathic surgery. The onlay grafts were used exclusively for cosmetic augmentation of facial defects without carrying loads.

A need exists for obtaining anchorage directly on parts of the jaws in order to allow the orthodontist the capability for moving teeth and bones in any direction. An anchorage device should be small, allow for various parts to fit into it for versatility of use, and be able to fit on bone and be applied to the bone surface only. If the anchorage device requires placement into bone, then it may be difficult to place the device in children because of potential damage to unerupted teeth. In addition, for cranial bone movements for cases of Crouzon's or Apert's syndrome for example, intra-bony devices may interrupt vital structures such as dura or sinusoids.

The objectives of this invention can be stated as follows:

1. It must not enter the bone but should attach to it;
2. it should be relatively thin to lay under soft tissue against bone, without creating significant inflammation;
3. it should have versatility of attachments in order to assume a role for an orthodontic anchor as well as an orthopedic anchor; and
4. it must have sufficient shear strength to absorb chewing forces and forces placed upon it from orthodontic loading.

SUMMARY OF THE INVENTION

An anchor system for treatment of growth disharmony and malalignment of teeth in which an onplant is surgically placed in a subperiosteal tunnel on the skeletal bone, allowing biointegration between the onplant bone interface and the bone, after which a palatal bar is attached to the anchor system, and the palatal bar is also attached to bands around two teeth, holding them non-mobile, permitting the orthodontist to treat the malalignment of the teeth.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein.

DESCRIPTION OF THE PREFERRED EMBODIMENTS

Figure 1:
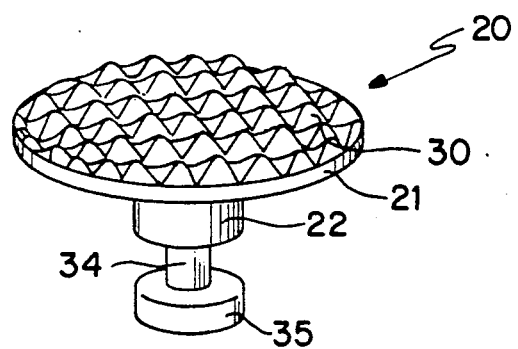
FIG. 1 is a perspective view of the invention.
Figure 2:
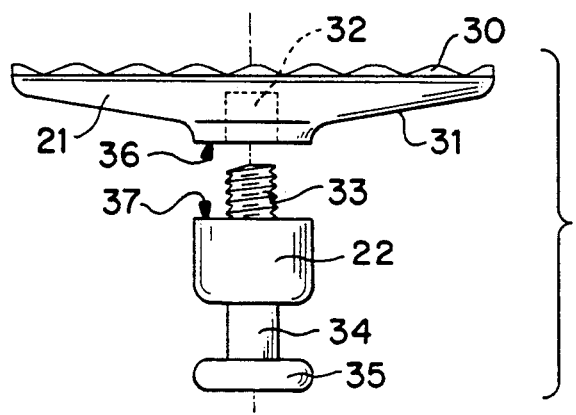
FIG. 2 is an exploded side elevation view of the invention of FIG. 1.
Figure 3:
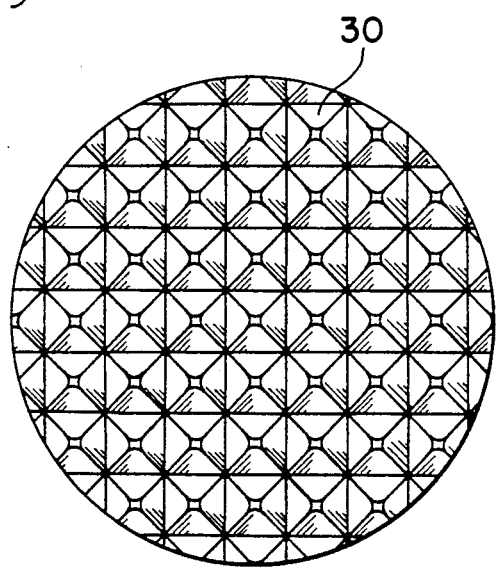
FIG. 3 is a top view of the invention of FIG. 1.
Figure 4:
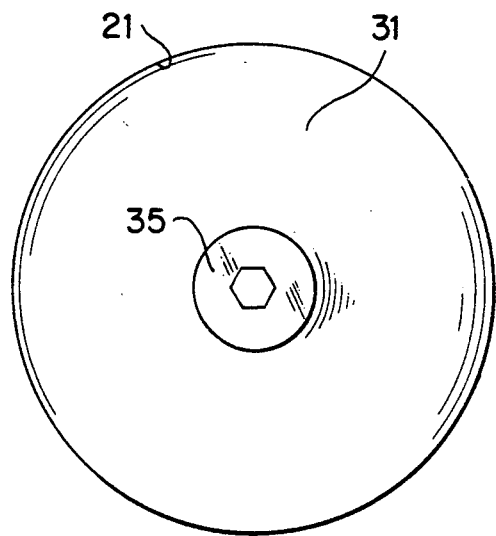
FIG. 4 is a bottom view of FIG. 1.

The orthodontic anchor system 20 has two parts; the onplant 21 and the abutment 22. These are connected to a palatal bar 24 or palatal wire 28, which is attached to bands 25 around the teeth to be held immobile.

As show in FIGS. 1–4 the onplant 20 has an circular upper surface which is the onplant bone interface 30. This onplant bone interface 30 is textured, which both increases the surface area and presents surface area which is better able to resist the shear forces imposed by the orthodontic anchor system 20. The textured onplant bone interface 30 is covered with hydroxylapatite.

The onplant 21 has a lower surface with a beveled outer portion 31 and a central circular portion 36. The outer portion 31 joins the outer periphery of the onplant bone interface 30. The center of the lower surface 36 has a threaded aperture 32. When the onplant 21 is initially installed the threaded aperture 32 has a healing screw 26, not shown, installed to prevent tissue from covering it and having to be removed.

The abutment 22 is circular, with an upper surface 37 matching the lower surface 36 of the onplant 21. The upper surface 37 has a protruding threaded screw 33 which cooperates with the threaded aperture 32. The abutment 22 has a neck 34 of reduced diameter and a head 35 of increased diameter, compared with the neck 34. Surface 35 as shown is illustrative only. It may have a slot, hexagonal, or threaded hole or other means of seating the abutment or attaching the palatal bar.

The dimensions of the onplant 21 may be 8 mm in diameter and 2 mm thickness. The abutment 22 may be 4 mm in overall height, with the neck 34 being 1 mm in height and 1 mm in diameter.

The structure of both the onplant 21 and the abutment 22 is a titanium alloy. The surface, except for the onplant bone interface 30, is smooth and all corners are beveled to prevent damage to soft tissue.

The test sample had a 50 micron coating of hydroxylapatite. It was plasma sprayed on the metal. The spray consists of a superheated solution of hydroxylapatite applied to the roughened titanium alloy.

Figure 5:
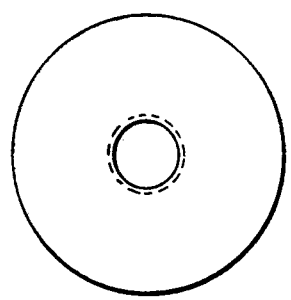
FIG. 5 is a bottom view of an alternative embodiment of the invention.

FIG. 5 shows a onplant 21 which is similar to the onplant 21 of FIG. 1. This onplant 21 is generally cylindrical in shape. It has the onplant bone interface 30 which is textured and coated by hydroxylapatite, and a threaded aperture 32.

Figure 6:
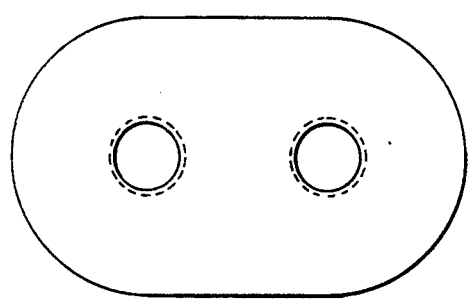
FIG. 6 is a bottom view of an alternative embodiment of the invention.

FIG. 6 is similar to FIG. 5, but is oval in shape and has two threaded apertures 32. This embodiment permits two orthodonic devices to be used.

Figure 7:
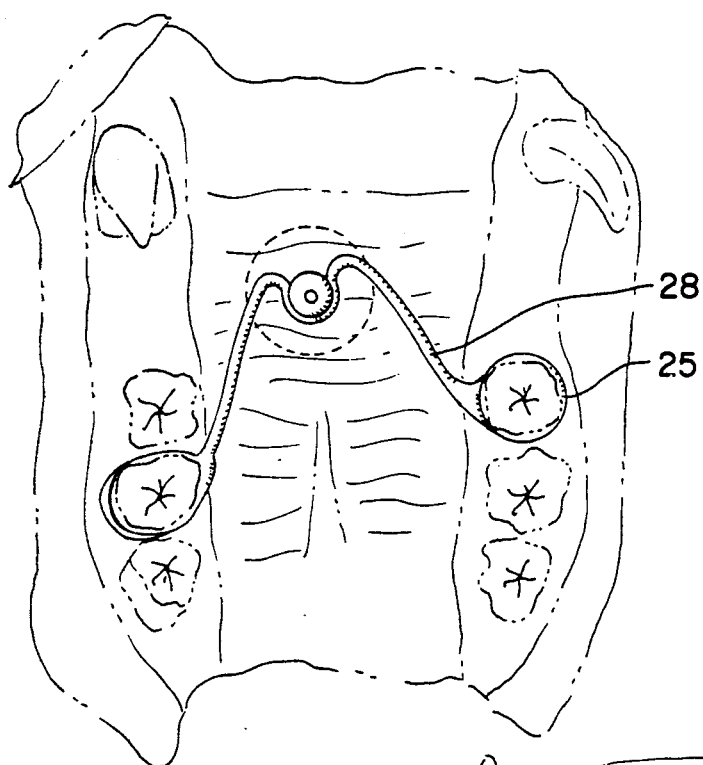
FIG. 7 is a bottom view with the orthodontic anchor system 20 installed in the roof of a mouth with the palatal wire 28 connected to two banded teeth.

As shown in FIG. 7 the palatal wire 28 is soldered to the two bands 25 of two molars or other teeth and presses into the neck 34 of the abutment 22, preventing the two teeth from moving forward. This palatal wire 28 may be fabricated from 0.051 in. orthodontic wire or cast from precious or non-precious metals.

Figure 8:
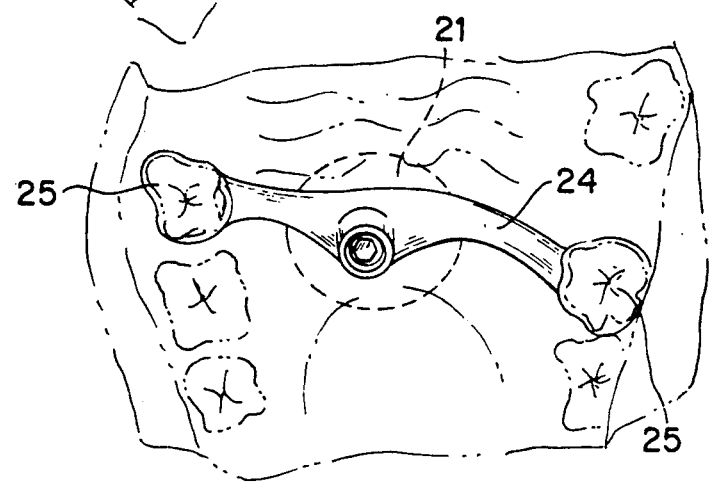
FIG. 8 is a bottom view with another orthodontic anchor system 20 installed in the roof of a mouth with the palatal bar 24 connected to two banded teeth.

FIG. 8 shows the orthodontic anchor system 20 mounted between the two teeth to be held stable. The palatal bar 24 is fabricated from thicker metal to resist the shear forces of the teeth against the orthodontic anchor system 20. This palatal bar 24 is screwed on abutment 22 which is screwed into the onplant 21.

The orthodontic anchor system 20 is able to resist both primary lateral and horizontal forces as well as a vertical force.

The orthodontic anchor system 20 is not limited to use with a palatal bar 24. It may alternatively be used with any conventional orthodontic device, as will be immediately apparent.

It is within the scope of the invention to use other suitable materials for the orthodontic anchor system 20. These will include inert metals, plastics and composites. Likewise the bonding means can be any mechanical means such as keylocks or miters or magnetic or biodegradable polymer. The onplant bone interface 30 may have a different textured surface or a non-textured surface which promotes adequate bonding strength. The thickness and method of applying the hydroxylapatite coating may be varied.

The orthodontic anchor system 20 is installed into a patient's mouth in accordance with the following procedures. These are generalized for an understanding of the invention, and are not the detailed procedures which would be actually followed by a surgeon.

Under local anaesthesia, an anterior palatal incision will be made and a subperiosteal tunnel created so that the tunnel will place the onplant at the proposed location (most likely between the permanent first molars). Conservative dissection will be used in order that palatal reflection is minimal and restricted to only the onplant site in order to prevent onplant migration. One or two onplants will be placed depending on the treatment needs for the patient.

Previous experience indicates that careful surgical technique will result in secure positioning of these onplants, without the need for retentive wires to maintain bone contact.

The onplant is usually provided sterile by the manufacturer. It will be placed into the subperiosteal tunnel taking great care to place it directly against the palatal bone. The incision will be closed using 4-0 polyglactin suture. The patients will be given a prescription for antibiotics (typically penicillin or doxycycline) and analgesics. This small surgical procedure should cause minimal pain to the patient. The patient will be called at home by the surgeon for follow up, and seen for suture removal one week after the surgery. The patient will be followed every two weeks for observation during the healing period which is necessary to achieve integration of the onplants hydroxylapatite surface with the underlying palatal bone.

Twelve weeks will be allowed for healing and biointegration to occur. Twelve weeks is the expected onplant biointegration time because that is the time required for integration of hydroxylapatite coated implants in humans. At twelve weeks, the patients will be given local anaesthesia and a small incision will be made directly over the onplant, exposing only the healing screw 26 that was placed into the internal thread of each device. An abutment 22 is then screwed into the onplant. The palatal tissue thickness may be thinned to 3 mm in order to allow for cleaning of the orthodontic device. An impression will be taken in order to fabricate a palatal bar 24 which is secured to the onplant and banded to the dentition.

The palatal wire 28 will be solid and minimally pliable. The wire will be soldered to bands glued to the anchor teeth. Approximately two weeks will be allowed for fabrication of the bar or bending the wire on a transferred study model. The wire will be fabricated of 0.051 in. orthodontic wire.

Two weeks later, orthodontic devices will be attached to the onplant and to the maxillary teeth, for example the first molar, placed in such a way that the wire attaching the onplant to the tooth acts to hold the tooth in position, as an anchor. The onplant will serve as the point of absolute anchorage, preventing the anchored teeth from moving anteriorly.

The remaining dentition will be treated with conventional orthodontic appliances. The location of the teeth with respect to the onplants may be measured and recorded both by radiographs and actual physical measurement with a Boley gauge.

At the conclusion of the treatment involving the device, under local anesthesia, an incision will be made exposing the entire onplant. Using a forcep designed for this procedure, the hydroxylapatite will be removed.

In a study investigating the difference between diameter and length on the ultimate pull-out strength of hydroxylapatite coated cylinders in the dog jaw, again a mechanically significant bonding was found with hydroxylapatite coated implants. In the dog alveolus in a cortical and cancellous bone environment, up to 45 pounds were required to pull hydroxylapatite coated onplants from the dog jaw. Based on these mechanical studies of onplants, we are confident that the onplant's hydroxylapatite bone bond can withstand continuously applied forces.

Hydroxylapatite coated implants can be used for restoration of partially and totally edentulous patients. Occlusal function has not resulted in loss of the hydroxylapatite coating, thus continuous occlusal function helps confirm our belief that a hydroxylapatite coated device can function under continuous load.

To further verify this concept, clinical trials of using hydroxylapatite coated dental implants as orthodontic anchor systems 20 (Hoffman, Block personal communication, 1989) demonstrate that one or two hydroxylapatite coated implants placed within the bone of the maxilla or mandible can be used as anchors for tooth movement. Teeth attached to the implants did not move whereas those teeth not attached to the implants moved noticeably when subjected to a similar force. Both in animal studies and in these clinical trials, these implants did not move, rather the teeth were moved when constant forces in excess of 11 ounces were continuously placed on the implants.

The anchor system may also be used as an orthopedic device. It may be attached to any appropriate bone, including any portion of the skeletal mass. It may be used to stabilize or anchor other devices such as a pacemaker, hearing aid, prothesis, or another bone. It may anchor external devices such as diagnostic or treatment devices.

This invention may also have similar application in veterinary medicine.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An orthodontic anchor system to cure malalignment of teeth which comprises in combination:
   a. an onplant which is surgically placed in the subperiosteal tunnel of a patient;
   b. said onplant having a onplant bone interface surface which is placed against the skeletal bone to permit biointegration;
   c. an orthodontic abutment which is attached to said onplant after biointegration has occurred between the onplant and the skeletal bone;
   d. an orthodontic device attached to two bands which are placed around two teeth and adapted to be attached to said onplant;
   whereby said orthodontic anchor system hold said teeth stable and non-mobile, permitting the orthodontist to treat the malalignment of the teeth of the patient.

2. The combination of claim 1 wherein the orthodontic device is a palatal bar.

3. The combination of claim 1 wherein said abutment is secured to the onplant after biointegration has occurred and said orthodontic device is a palatal wire attached to the abutment.

4. The combination of claim 3 wherein the abutment has a neck of reduced diameter between its upper surface and a head and the palatal wire fits against the neck.

* * * * *